United States Patent [19]
Reed

[11] Patent Number: 5,559,605
[45] Date of Patent: Sep. 24, 1996

[54] METHOD AND APPARATUS FOR DETERMINING DIRECTIONAL VARIATION OF SHADE OF PILE AND NAPPED MATERIALS

[75] Inventor: Morton W. Reed, LaGrange, Ga.

[73] Assignee: Milliken Research Corporation, Spartanburg, S.C.

[21] Appl. No.: 391,311

[22] Filed: Feb. 17, 1995

Related U.S. Application Data

[63] Continuation of Ser. No. 174,984, Dec. 29, 1993, abandoned.

[51] Int. Cl.⁶ ..................................................... G01J 3/46
[52] U.S. Cl. .................... 356/402; 356/319; 356/326; 250/226; 385/12
[58] Field of Search ..................... 356/319, 402–411, 356/429, 445–448, 326; 385/31, 147, 90, 12, 13; 250/226, 560, 559.19, 559.2, 559.39, 559.4, 548

[56] References Cited

U.S. PATENT DOCUMENTS

| | | | |
|---|---|---|---|
| 3,663,108 | 5/1972 | Yamamuro et al. | 356/429 |
| 4,029,419 | 6/1977 | Schumann | 356/446 |
| 4,371,576 | 2/1983 | Machell | 428/92 |
| 4,576,665 | 3/1986 | Machell | 156/72 |
| 4,578,554 | 3/1986 | Coulter | 219/121 LC |
| 4,707,138 | 11/1987 | Coatney | 356/402 |
| 4,917,500 | 4/1990 | Lugos | 356/402 |
| 5,151,751 | 9/1992 | Nakajima et al. | 356/402 |
| 5,233,408 | 8/1993 | Satula | 356/402 |

FOREIGN PATENT DOCUMENTS

| | | | |
|---|---|---|---|
| 24256 | 12/1986 | Japan . | |
| 180117 | 10/1989 | Japan | 356/402 |

OTHER PUBLICATIONS

Simon, "Shade Sorting by the 555 System", Mar. 1984, American Dye Stuff Reporter, pp. 17–28.

*Primary Examiner*—K. Hantis
*Attorney, Agent, or Firm*—Terry T. Moyer; Kevin M. Kercher

[57] ABSTRACT

This invention relates to a method and apparatus for determining directional variation of shade of pile or napped materials. This directional variation of shade can be determined in multiple directions either simultaneously or sequentially utilizing spectrophotometers with bifurcated fiber optic cables. The bifurcated fiber optic cable is repeatably and accurately positioned over the pile or napped materials. A typical non-limiting example of pile materials includes carpeting.

37 Claims, 10 Drawing Sheets

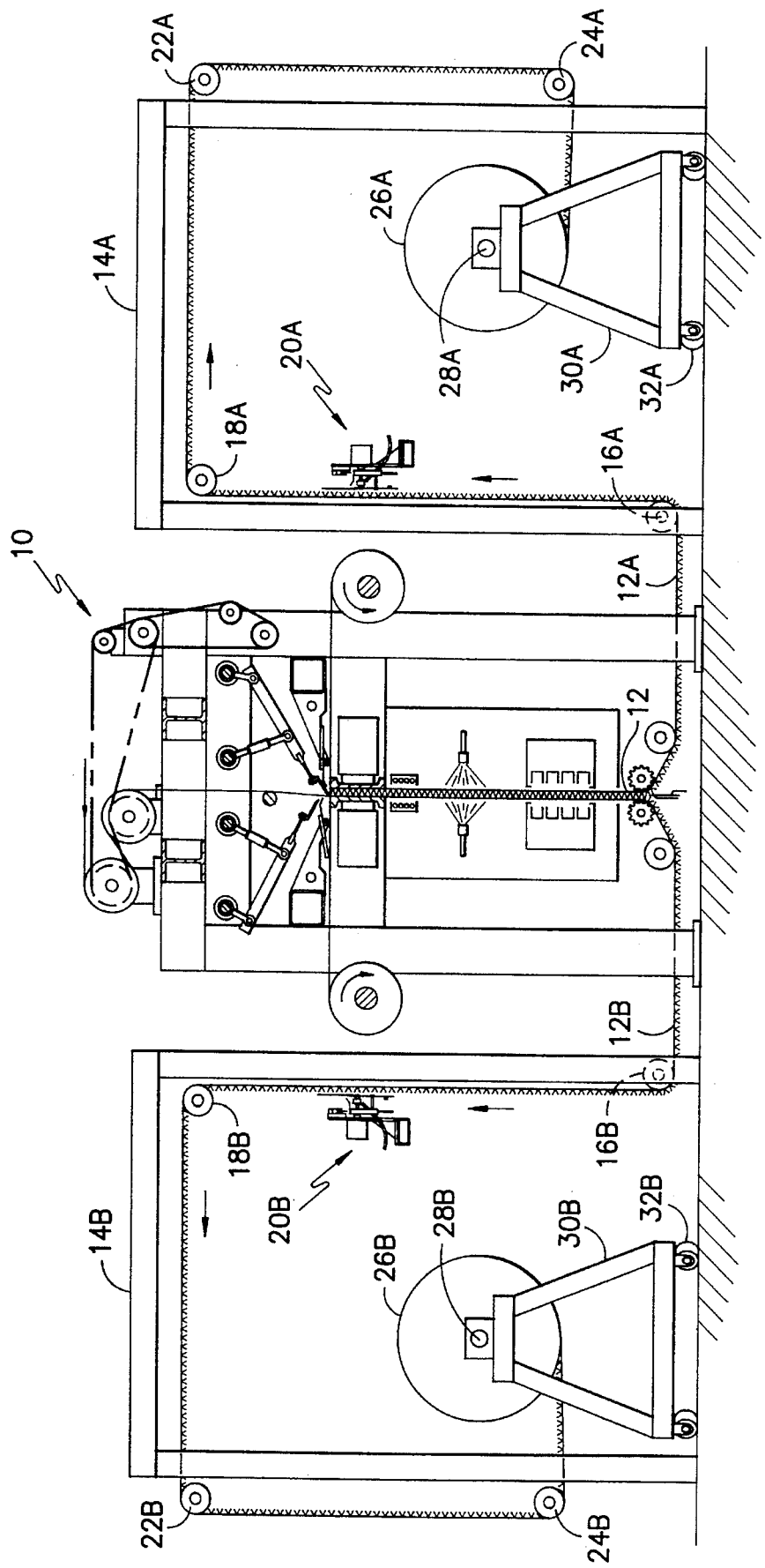
FIG. -1-

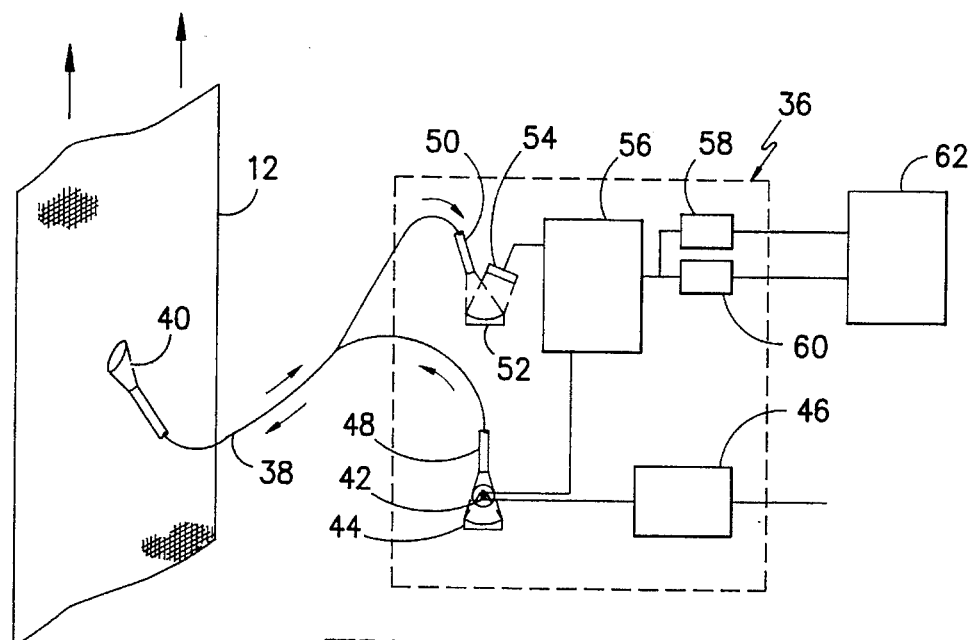
FIG. -2-
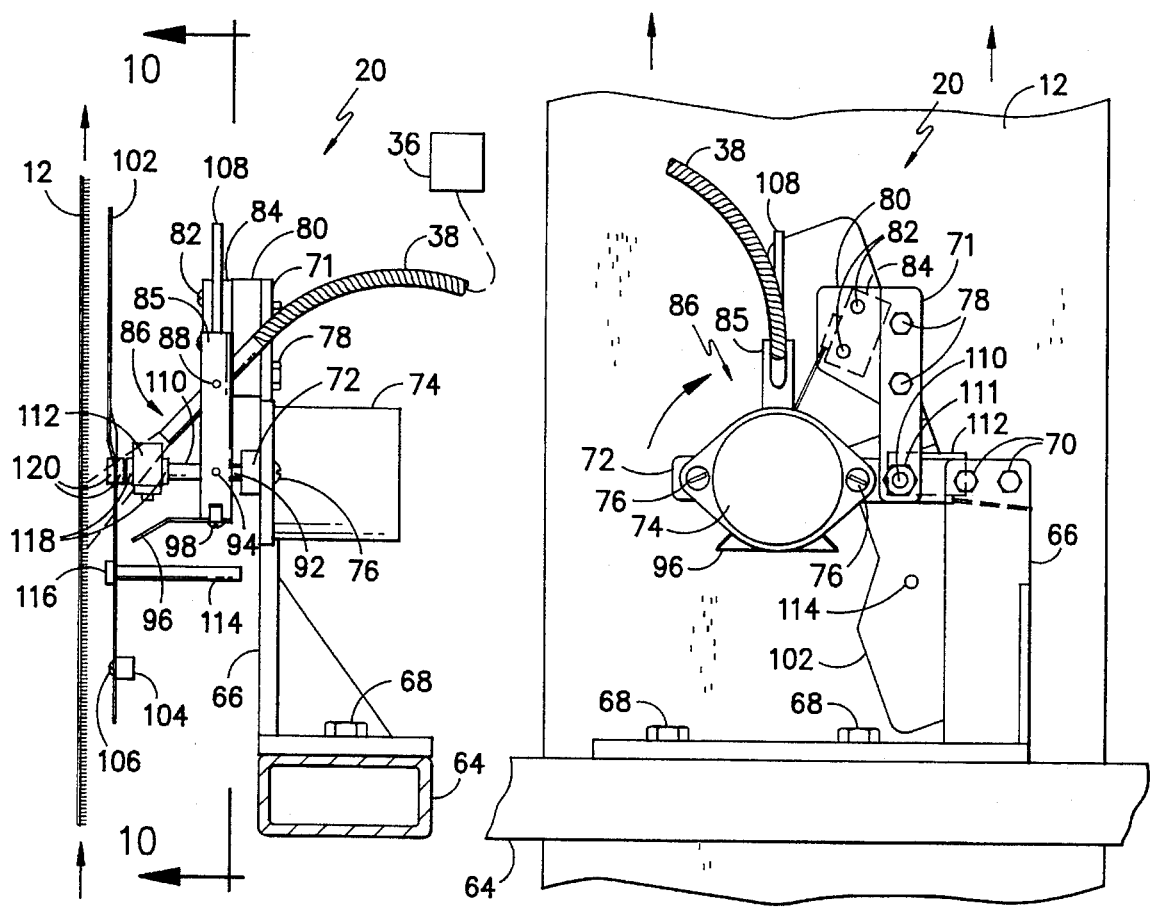
FIG. -4-   FIG. -3-

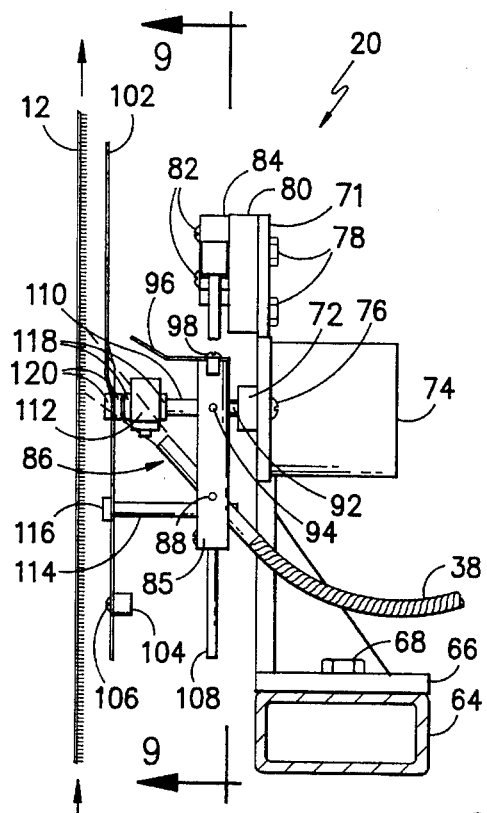
FIG. -6-
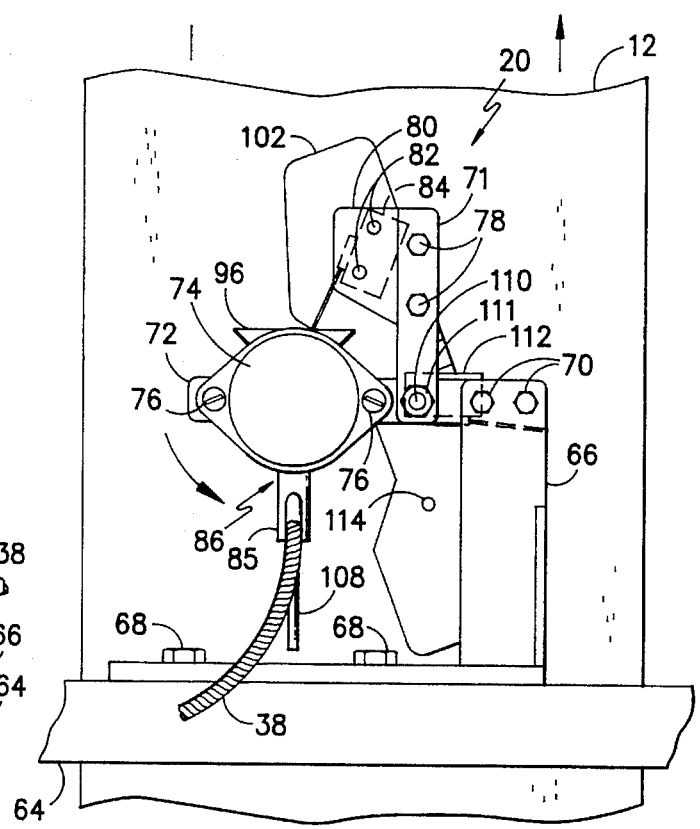
FIG. -5-
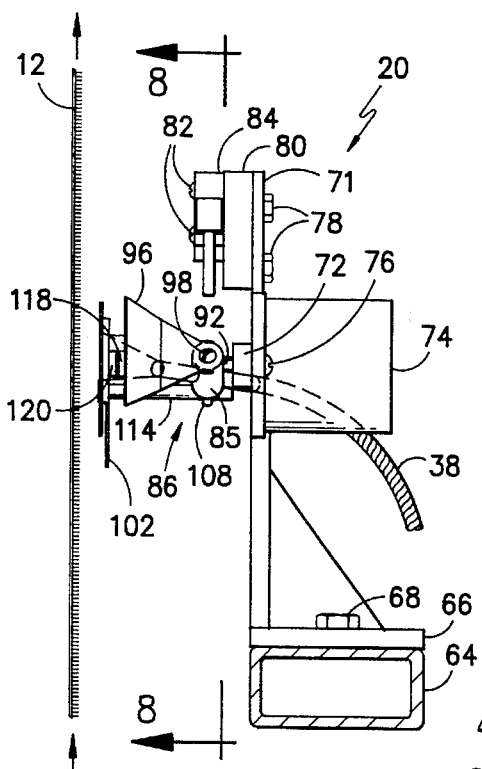
FIG. -8-
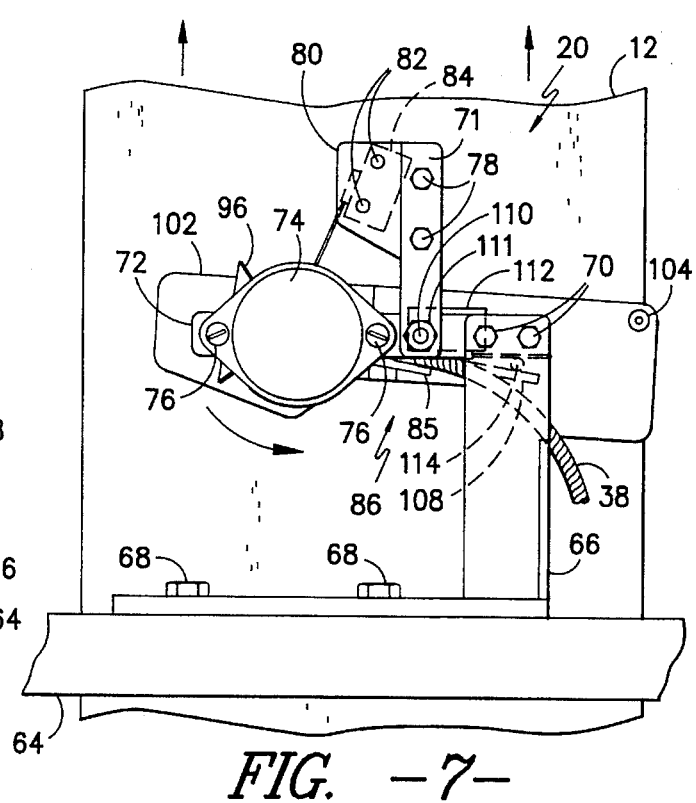
FIG. -7-

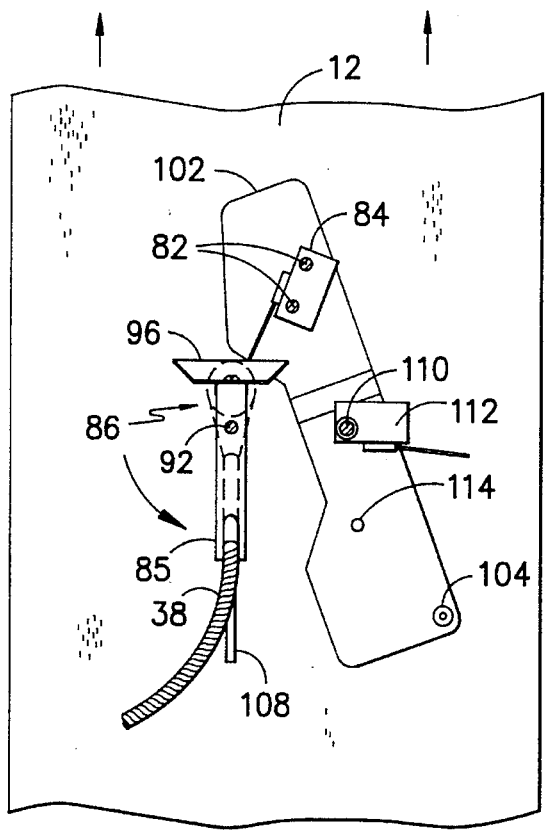
FIG. -9-
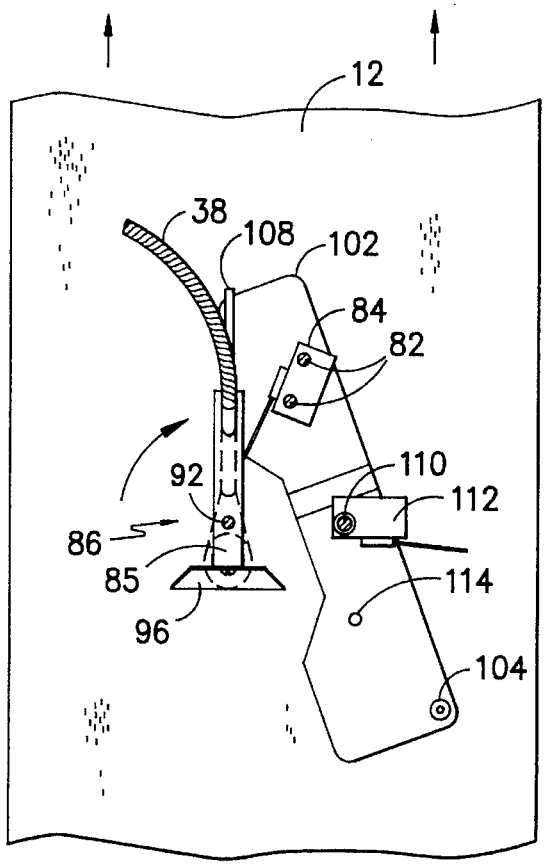
FIG. -10-
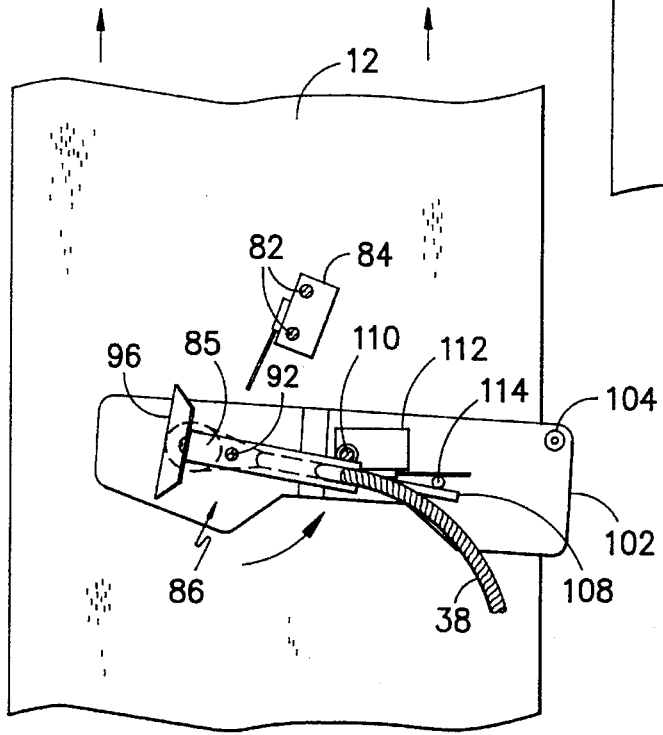
FIG. -11-

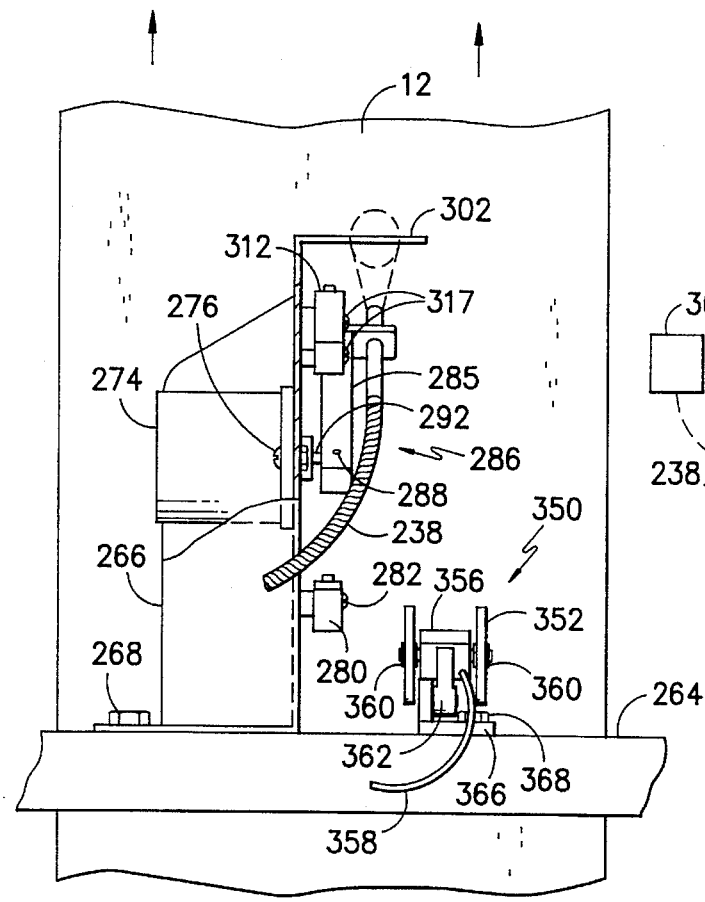
FIG. -12-
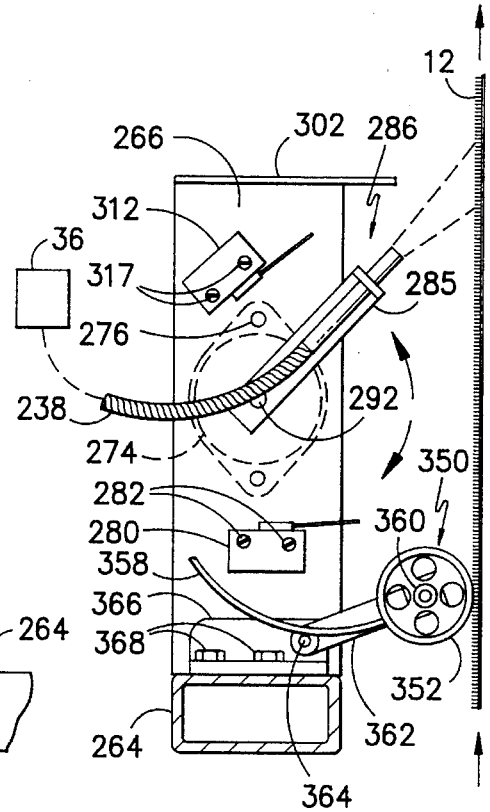
FIG. -13-
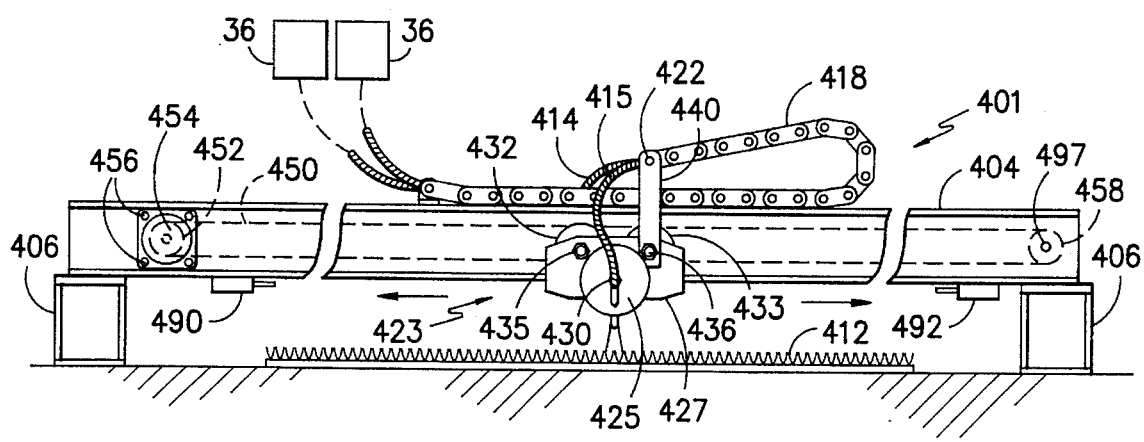
FIG. -14-

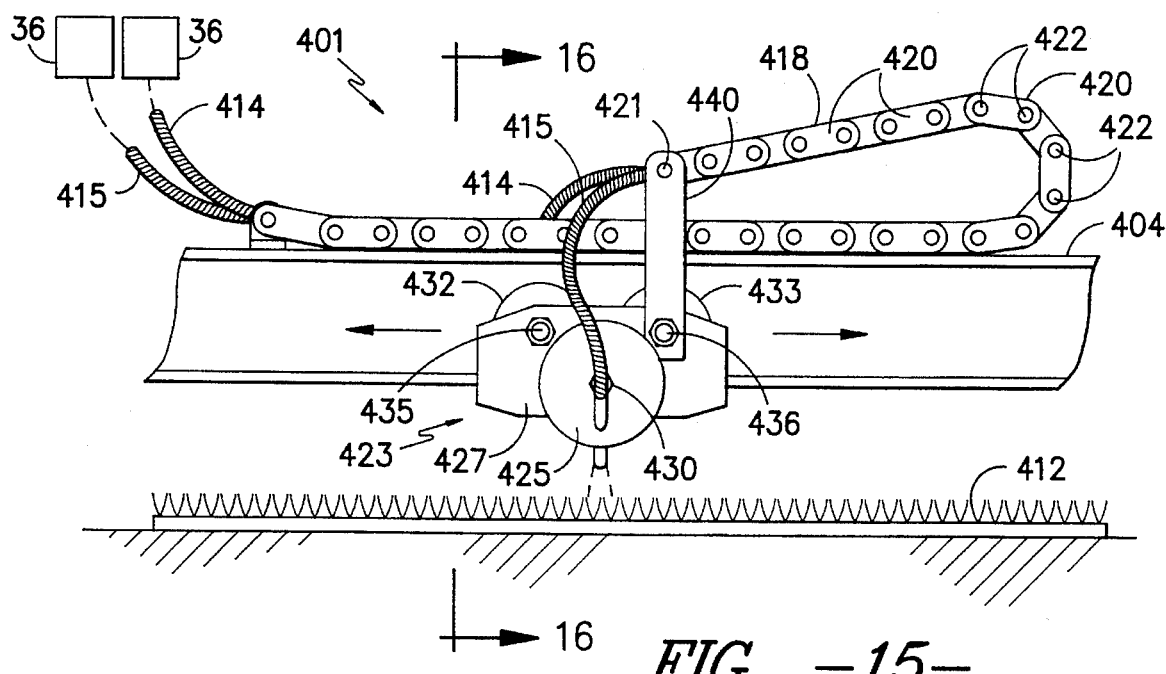
FIG. -15-
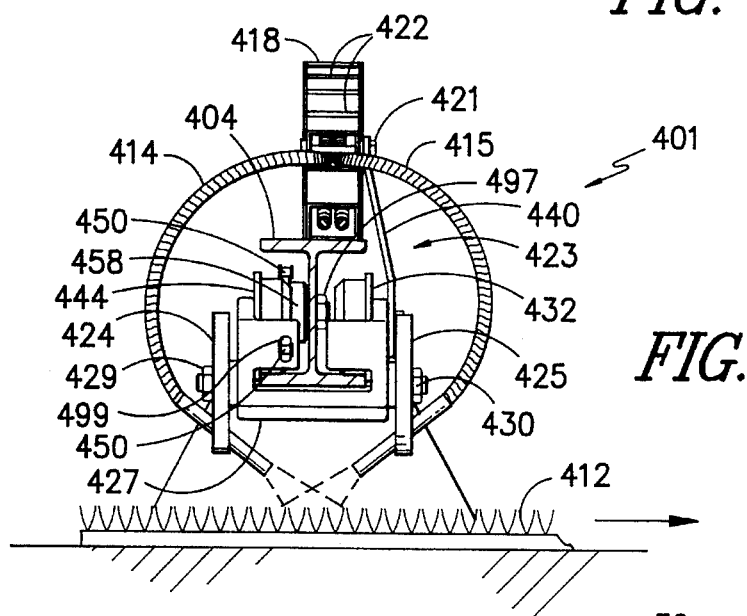
FIG. -16-
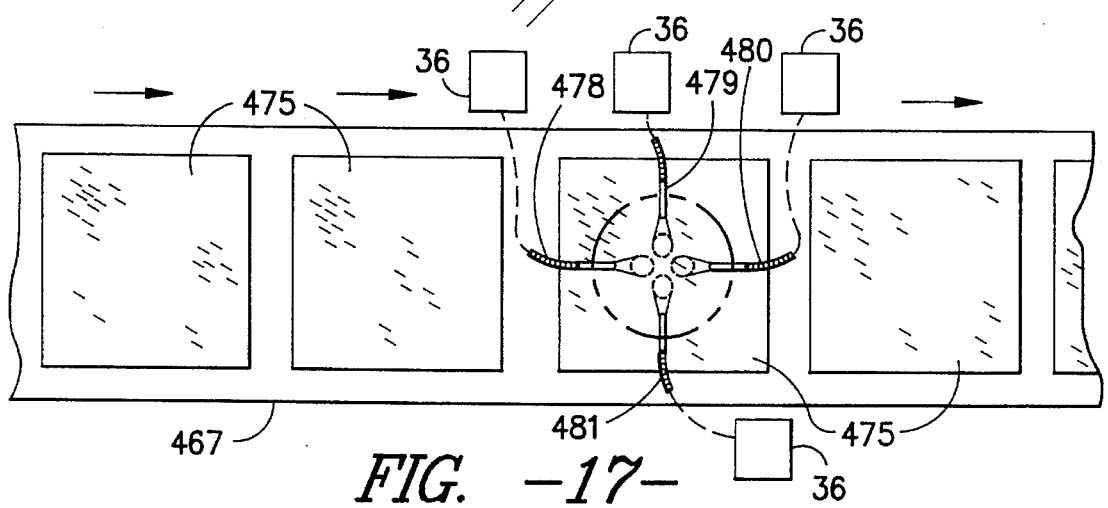
FIG. -17-

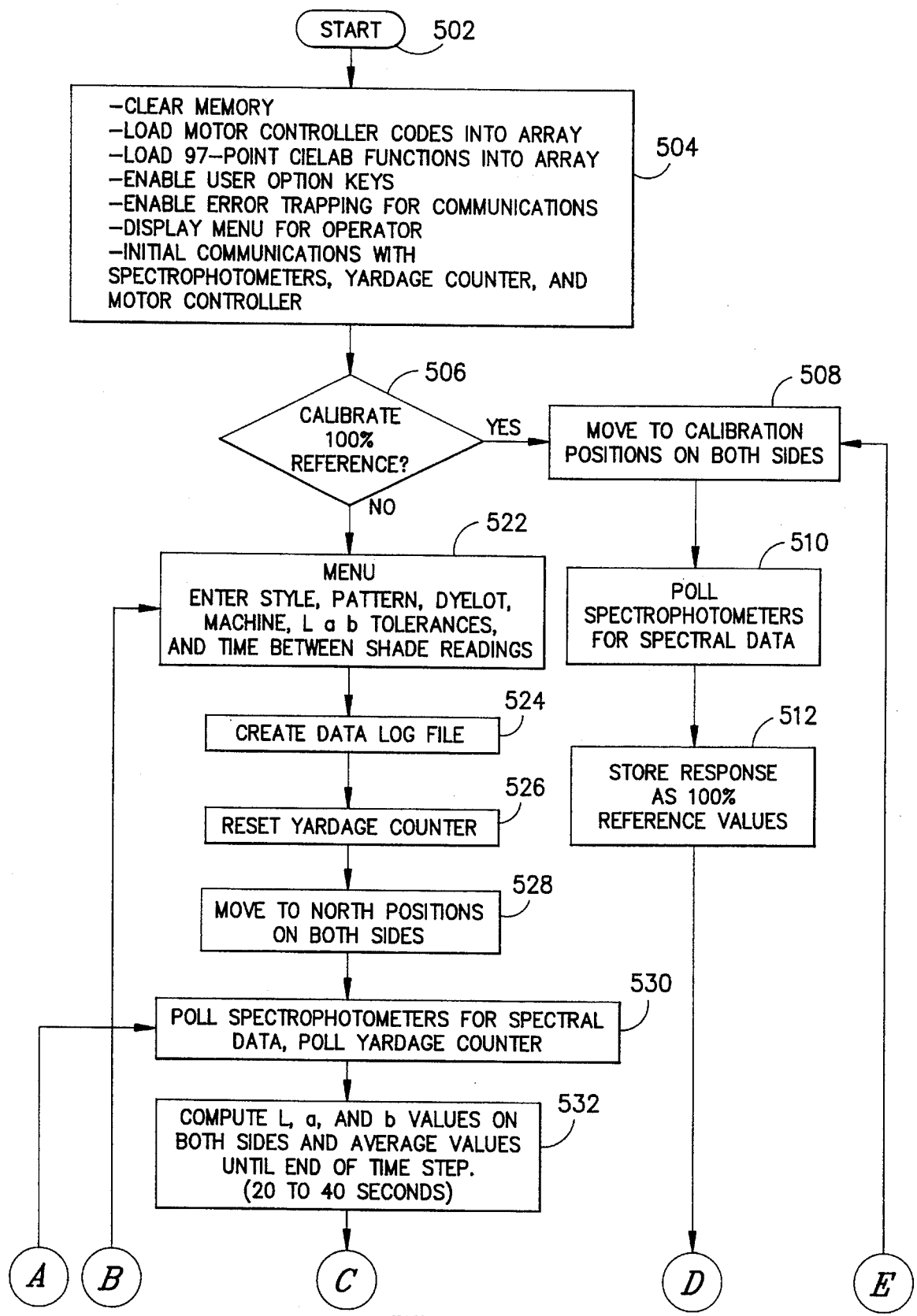
FIG. −18−

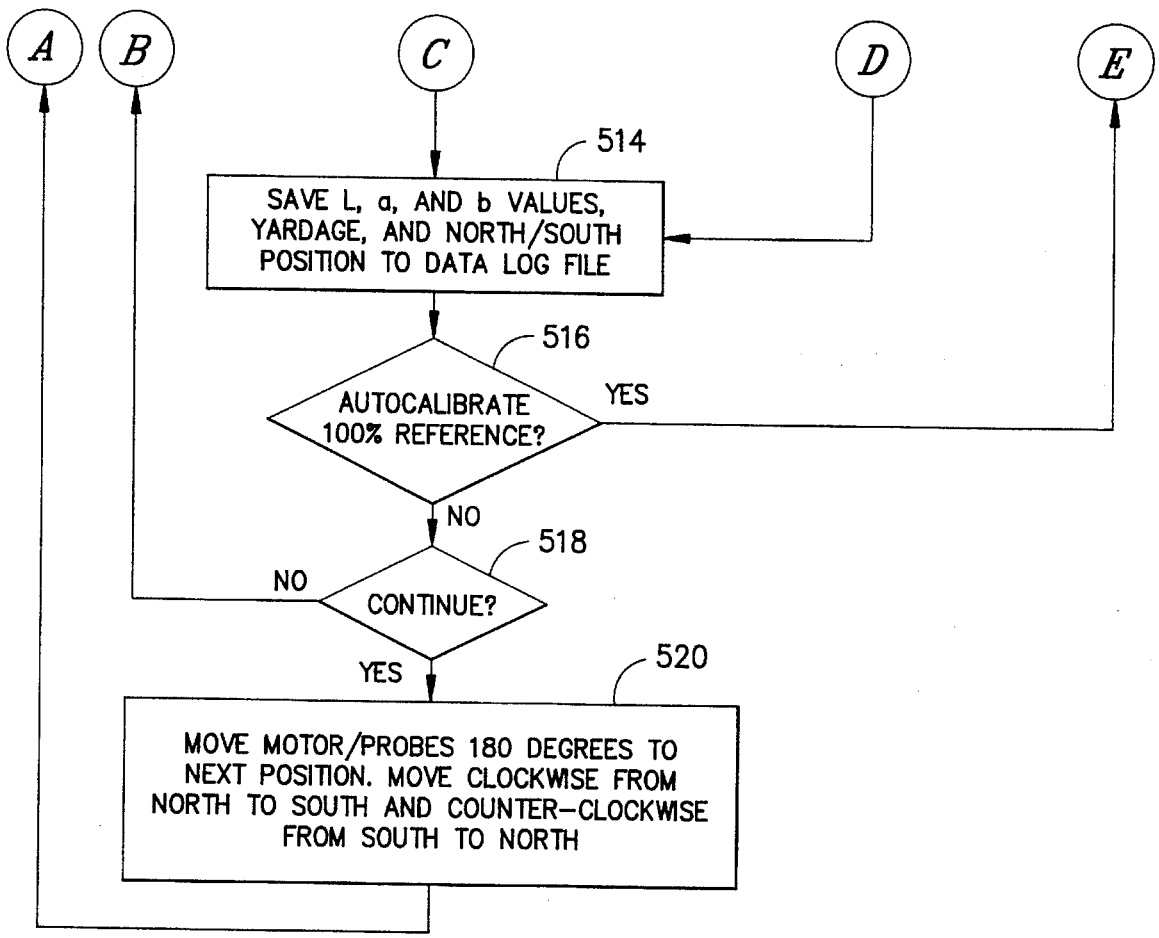
FIG. -19-

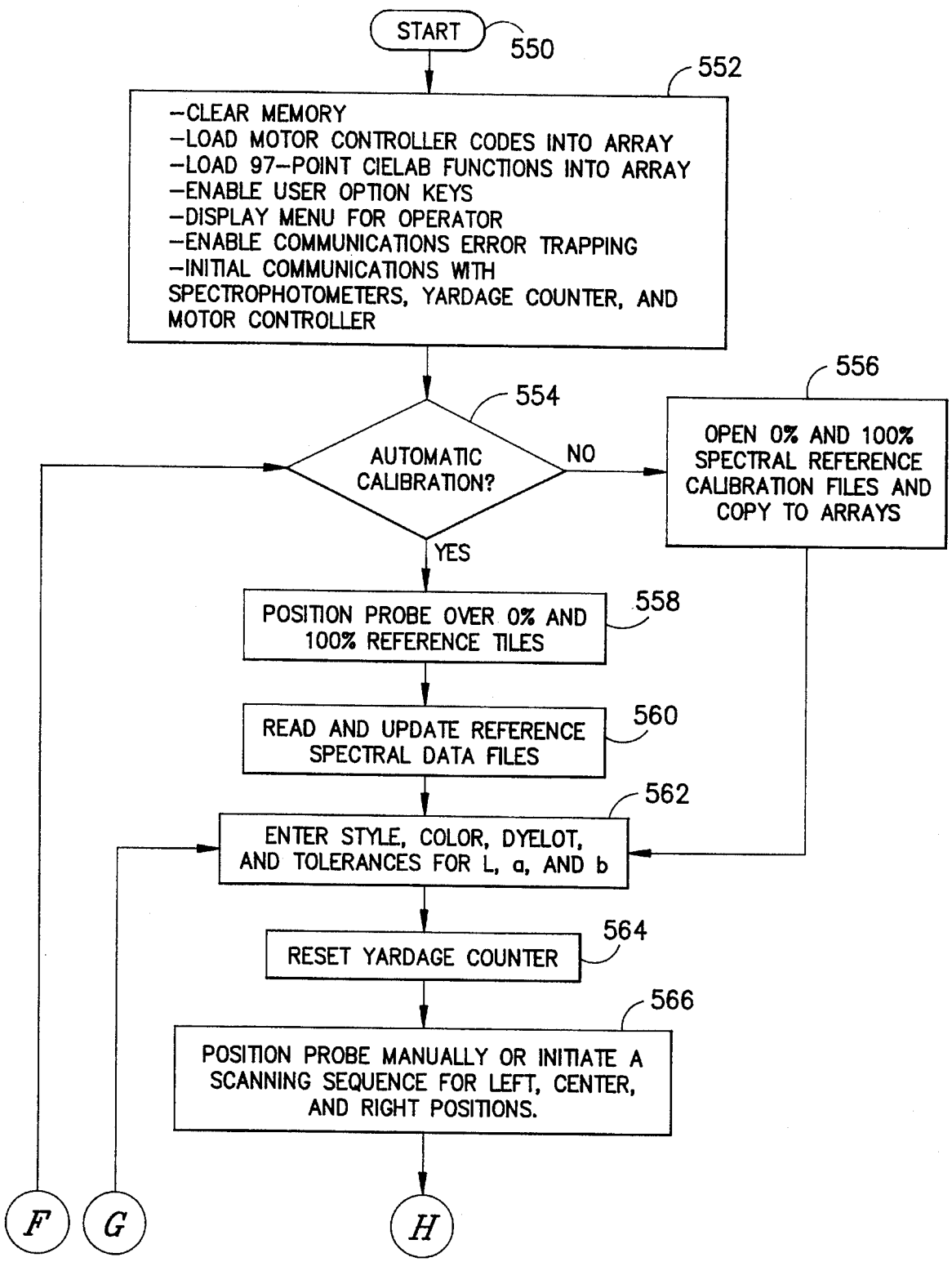
FIG. —20—

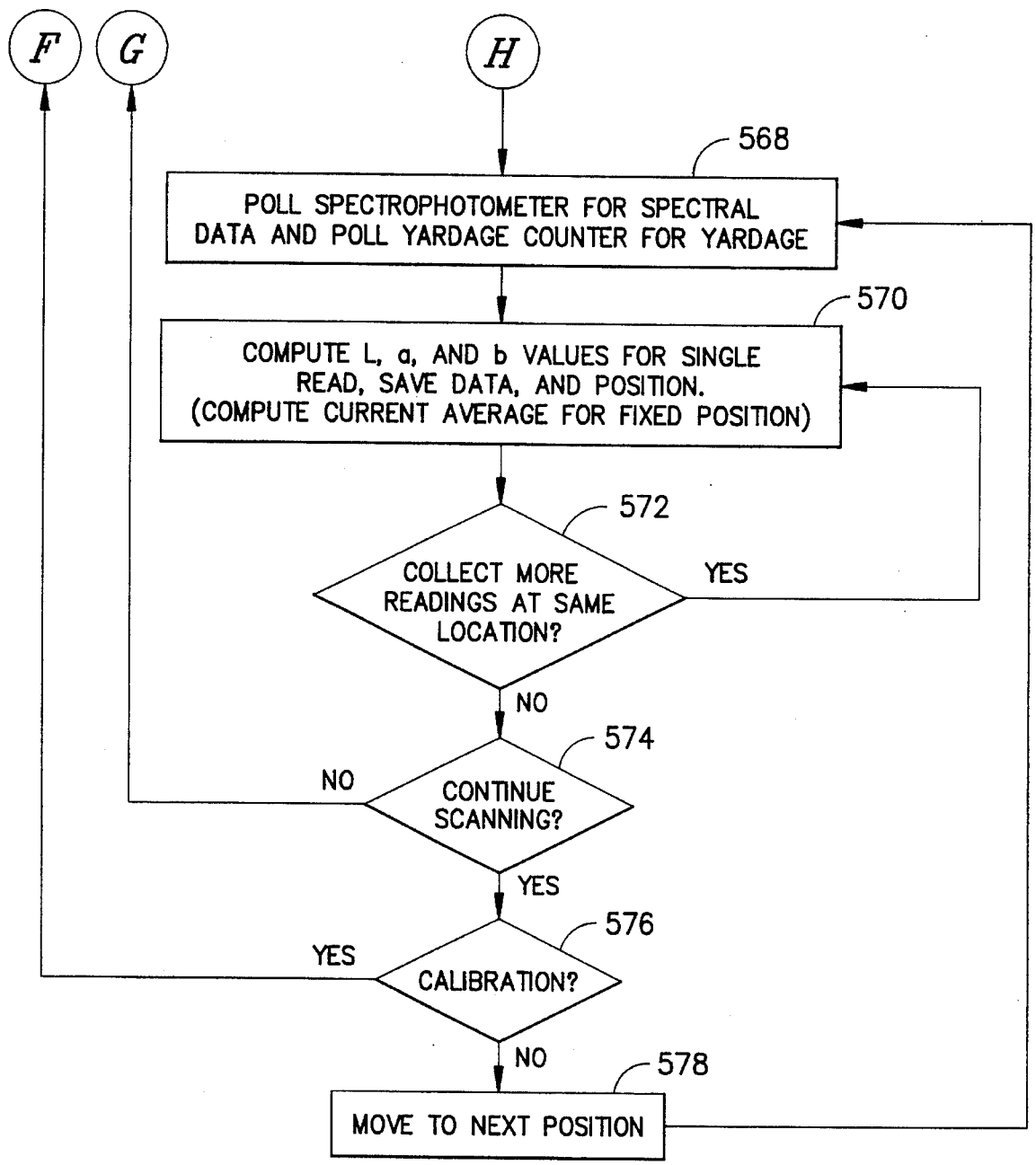
FIG. -21-

5,559,605

METHOD AND APPARATUS FOR DETERMINING DIRECTIONAL VARIATION OF SHADE OF PILE AND NAPPED MATERIALS

This application is a continuation of U.S. patent application Ser. No. 08/174,984, filed Dec. 29, 1993, now abandoned, by Morton Wallace Reed entitled METHOD AND APPARATUS FOR DETERMINING DIRECTIONAL VARIATION OF SHADE OF PILE AND NAPPED MATERIALS.

BACKGROUND OF THE INVENTION

Unlike flat goods such as woven or knitted fabrics, there is a significant variation in shade for pile and napped textile materials when viewed from all four directions. A non-limiting example of pile fabrics includes carpeting. Shade is determined in terms of either color hue, chroma or C.I.E. laboratory values. Traditionally, the measurement of shade of pile and napped materials is accomplished by determining color by utilizing a spectrophotometer to read color from a single fixed position. There are several kinds of spectrophotometers that use either a "0/45" or a "45/0" geometry. This requires the pile to be compressed under a glass plate since the sample is observed from a fixed angle of either zero or forty-five degrees. There are also geometries that are classed as "0/0" meaning that the viewing and illuminating angles are the same and compression of the pile is optional. However, no attempt to use robotically-moveable bifurcated fiber-optic cables with "0/0" type spectrophotometers exists. Furthermore, the size, cost, and complexity of the present textile shade monitors that are capable of reading in a "0/0" direction has prevented their use for directional shade measurement. The directivity of shade is then estimated by measuring the pile angle of the textile material and determining the pile height of the textile material and then developing statistical correlations. This is a very complicated and time consuming approximation that is inaccurate due to the failure of mathematical models to account for actual material and colorant variation. The present invention solves these problems in a manner not disclosed in the known prior art.

SUMMARY OF THE INVENTION

This invention relates to a method and apparatus for determining directional variation of shade of pile or napped materials. This directional variation of shade can be determined in multiple directional either simultaneously or sequentially utilizing spectrophotometers with bifurcated fiber optic cables. The bifurcated fiber optic cable is repeatably and accurately positioned over the pile or napped materials. A typical non-limiting example of pile materials includes carpeting.

It is an advantage of this invention to provide directional textile shade measurement for pile or napped materials.

Still another advantage of this invention is that the need to determine pile angle and pile height in conjunction with complex statistical shade correlations to estimate directional textile color measurement is eliminated.

Another advantage of this invention is that the on-line determination of directional textile shade measurement of pile or napped materials while in production is possible.

These and other advantages will be in part apparent and in part pointed out below.

BRIEF DESCRIPTION OF THE DRAWINGS

The above as well as other objects of the invention will become more apparent from the following detailed description of the preferred embodiments of the invention when taken together with the accompanying drawings, in which:

FIG. 1 schematically depicts an elevational view of an apparatus embodying the invention which is utilized in a dual capacity with a typical carpet bonding machine to provide directional textile shade measurement;

FIG. 2 is a schematic view of an apparatus embodying the invention utilizing a spectrophotometer and a robotically moveable bifurcated fiber optic cable to make directional textile shade measurements on a piece of carpeting;

FIG. 3 is a top plan view of the directional textile shade measurement device of the present invention in which the bifurcated fiber optic cable is directed downward against the direction of movement of a continuous web of carpeting;

FIG. 4 is a side elevational view of the directional textile shade measurement device of the present invention, corresponding to FIG. 3, in which the bifurcated fiber optic cable is directed downward against the direction of movement of a continuous web of carpeting;

FIG. 5 is a top plan view of the directional textile shade measurement device of the present invention in which the bifurcated fiber optic cable is directed upward in the direction of movement of a continuous web of carpeting;

FIG. 6 is a side elevational view of the directional textile shade measurement device of the present invention, corresponding to FIG. 5, in which the bifurcated fiber optic cable is directed upward in the direction of movement of a continuous web of carpeting;

FIG. 7 is a top plan view of the directional textile shade measurement device of the present invention in which the bifurcated fiber optic cable image is directed against a reference plate;

FIG. 8 is a side elevational view of the directional textile shade measurement device of the present invention, corresponding to FIG. 7, in which the bifurcated fiber optic cable image directed against a reference plate;

FIG. 9 is a cross-sectional view taken on line 9—9 of FIG. 6;

FIG. 10 is a cross-sectional view taken on line 10—10 of FIG. 4;

FIG. 11 is a cross-sectional view taken on line 11—11 of FIG. 8;

FIG. 12 is a top plan view of an alternative embodiment of the directional textile shade measurement device of the present invention in which the bifurcated fiber optic cable image is directed upward in the direction of movement of a continuous web of carpeting;

FIG. 13 is a side elevational view of the alternative embodiment of a directional textile shade measurement device of the present invention, corresponding to FIG. 12, in which the bifurcated fiber optic cable is directed upward in the direction of movement of a continuous web of carpeting;

FIG. 14 is a side elevational view of an alternative embodiment of the directional textile shade measurement device of the present invention utilizing two bifurcated fiber optic cables to measure shade in two directions while scanning broadloom carpet and/or other large pieces of pile or napped material;

FIG. 15 is an isolated side elevational view of the alternative embodiment of the directional textile shade measurement device of the present invention, as shown in FIG. 14, utilizing two bifurcated fiber optic cables to measure shade in two directions while scanning broadloom carpet and/or other large pieces of pile or napped material;

FIG. 16 is a cross-sectional view taken on line 16—16 of FIG. 15;

FIG. 17 is a isolated plan view of an alternative embodiment of the directional textile shade measurement device of the present invention, as shown in FIG. 14, utilizing four bifurcated fiber optic cables to measure shade in four directions for carpeting and/or other pile or napped materials;

FIG. 18 is a flow chart detailing the process steps in monitoring shade in two directions on either side of an on-line carpet bonding machine as shown in FIG. 1;

FIG. 19 is a continuation of the flow chart of FIG. 18, detailing the process steps in monitoring shade in two directions on either side of an on-line carpet bonding machine as shown in FIG. 1;

FIG. 20 is a flow chart detailing the process steps in monitoring shade in two directions while scanning an on-line broadloom carpet range as shown in FIG. 14; and FIG. 21 is a continuation of the flow chart of FIG. 20, detailing the process steps in monitoring shade in two directions while scanning an on-line broadloom carpet range as shown in FIG. 14.

Corresponding reference characters indicate corresponding parts throughout the several views of the drawings.

DETAILED DESCRIPTION OF THE PREFERRED EMBODIMENT

Referring now to the accompanying drawings, and initially to FIG. 1, which discloses an apparatus for generating bonded pile fabrics, generally indicated by numeral 10. Additional information relating to the bonding of pile fabric, can be found in coassigned U.S. Pat. No. 4,371,576, that issued on Feb. 1, 1983, which is incorporated by reference as if fully set forth herein and coassigned U.S. Pat. No. 4,576,665, that issued on Mar. 18, 1986, which is incorporated by reference as if fully set forth herein.

After the bonded pile fabric 12 is slit into two components, bonded pile fabric 12A enters shade measuring frame 14A and is directed vertically upward by idler roll 16A past the shade measuring apparatus of the present invention that is generally indicated by numeral 20A. The bonded pile fabric 12A is then directed horizontally across the top of the shade measuring frame 14A by idler roll 18A and then vertically downward by idler roll 22A. Bonded pile fabric 12A is then feed horizontally into take-up roll 26A by means of idler roll 24A. Take-up roll 26A is attached to axle 28A that is rotatably mounted on frame 30A. Frame 30A can be mounted on casters 32A for removing the take-up roll 26A when it is full of bonded pile fabric, e.g., carpeting.

This situation is replicated for the bonded pile fabric 12B in exactly the same manner as for the bonded pile fabric 12A. Bonded pile fabric 12B enters shade measuring frame 14B and is directed vertically upward by idler roll 16B past the shade measuring apparatus of the present invention that is generally indicated by numeral 20B. The bonded pile fabric 12B is then directed horizontally across the top of the shade measuring frame 14B by idler roll 18B and then vertically downward by idler roll 22B. Bonded pile fabric 12B is then feed horizontally into take-up roll 26B by means of idler roll 24B. Take-up roll 26B is attached to axle 28B that is rotatably mounted on frame 30B. Frame 30B can be mounted on casters 32B for removing the take-up roll 26B when it is full of bonded pile fabric, e.g., carpeting. This procedure is technically known as "doffing". The shade measuring apparatus 20A or 20B can measure shade of bonded pile fabric 12A or 12B located in the horizontal plane in the same manner as described above for the vertical plane.

Referring now to FIG. 2, a spectrophotometer system is generally indicated by numeral 36. A bifurcated fiber optic cable 38 shines light 40 on the pile or napped fabric 12, e.g. carpeting, by means of a lamp assembly or flash tube 42 that shines light against a mirror 44 and into the output strands 48 of the bifurcated fiber optic cable 38. The reflected light 40 from the pile or napped fabric 12 then passes back into the bifurcated fiber optic cable 38 and into the bifurcated fiber optic input 50 to reflect against a diffraction grating 52 that separates the light 40 into a spectrum of colors having a wavelength ranging between three hundred and fifty nanometers and seven hundred and fifty nanometers with the intensity of the spectrum affecting a photo diode array 54. A typical photo diode array 54 has over one hundred photo diodes or pixels. This shade information is then stored in registers by a microprocessor controller 56 and is sent on command to the host computer 62 by means of either an RS-232C communications port 58 or an RS-485 communications port 60. The lamp assembly or flash tube 42 and a microprocessor controller 56 are powered by a power supply 46.

Typical manufacturers of diode array spectrophotometers include Honeywell Microswitch Division, located at 117 Perimeter Center West, Suite 3301, Atlanta, Ga. 30338-5426 and Hewlett Packard Gmbtt, Hewlett-Packard-Str, D-7517 Waldronn 2, Germany. Typical manufacturers of bifurcated fiber optic cables include Honeywell Microswitch Division, located at 117 Perimeter Center West, Suite 3301, Atlanta, Ga. 30338-5426 and Banner Engineering Corporation, P.O. Box 9414, Minneapolis, Minn., 55440. A typical host computer system can be any of a wide range of commercially available state of the art components utilizing virtually any operating system with the preferred computer being a graphics work station connected to a process control network.

Referring now to FIGS. 3, 4, 5, 6, 7 and 8, the shade measuring apparatus of the present invention is generally indicated by numeral 20 positioned over the pile or napped fabric 12, e.g., carpeting. There is a shade measuring support bracket indicated by numeral 64 having an L-shaped bracket 66 attached thereto by means of a first pair of bolts 68.

There is a second pair of bolts 70 that attach the L-shaped bracket 66 to a stepper motor support bracket 72. The stepper motor 74 is fixedly attached to the stepper motor support bracket 72 by means of a third pair of bolts 76. Typical manufacturers of stepper motors include Arrick Robotics located at P.O. Box 1574, Hurst, Tex. 76053 and Research Designs, Inc. located at 4760 Hammermill Road, Building 206, Tucker, Ga. and Cyber Research, Inc. located at 25 Business Park Drive, Branford, Conn. 06405. There is a limit switch support bracket 71 that is attached to a first limit switch plate 80 by means of a fourth pair of bolts 78. The first limit switch 84 is attached to the first limit switch plate 80 by means of a fifth pair of bolts 82. A bolt 110 secures limit switch support bracket 71 to stepper motor support bracket 72 with the associated nut 111. Bolt 110 passes through a second limit switch 112 and is secured by a pair of nuts 118. There is a pair of lugs 120 at the end of the bolt 110 that secures a calibration plate 102 in position while allowing rotation thereof.

There is a bifurcated fiber optic cable 38 that can be positioned at a fixed angle or a plurality of fixed angles in relation to the pile or napped fabric 12, e.g., carpeting, by any of a wide variety of mechanical support means. A specific example of a positioning member to support the bifurcated fiber optic cable 38 is that disclosed in FIGS. 3, 4, 5, 6, 7 and 8 and is generally indicated by numeral 86. The angle of the bifurcated fiber optic cable 38 can be varied in two ways at the same time in a true goniospectrophotometric manner. In the plane of the pile or napped fabric 12, e.g., carpeting, any direction from zero to three hundred and sixty degrees can be scanned. In the normal plane to the pile or napped fabric 12, angles from zero to one hundred and eighty degrees can be selected. Preferably, the shade measuring apparatus 20 utilizes a plus or minus forty-five degree angle from the normal and is rotated by computer control through an oscillating arc from zero to one hundred and eighty degrees or from zero to three hundred and sixty degrees depending on the method of placing the calibration plate 102. Additional motors can be utilized to add scanning ability across the width of the pile or napped fabric 12, e.g., carpeting.

The bifurcated fiber optic cable 38 is rotatably connected to the stepper motor 74 by means of a positioning bracket 85. The bifurcated fiber optic cable 38 is fixedly attached to a positioning bracket 85 by means of a first set screw 88. Projecting from the stepper motor 74 is a rotatable axle 92. The rotatable axle 92 is fixedly attached to the positioning bracket 85 by means of a second set screw 94. Attached to the front of the positioning bracket 85 is a metal shield 96 for deflecting lint and other fibrous debris. The metal shield 96 is attached to the positioning bracket 85 by means of a screw 98.

The calibration plate 102, as previously described, can be positioned in front of the bifurcated fiber optic cable 38. The calibration plate 102 has a counterweight 104 located thereon that is attached by means of a counterweight screw 106.

There is a positioning lever 108 that is attached to the positioning bracket 85 at the end that is opposite the metal shield 96. The calibration plate 102 can be moved by contacting a position pole 114 with the positioning lever 108. The position pole 114 is attached to the calibration plate 102 by means of an attachment bolt 116. Movement of the calibration plate 102 ceases when the calibration plate 102 contacts the second limit switch 112 that is held in position by dual nuts 118 on bolt 110. Bolt 110 passes through limit switch support bracket 71 and stepper motor support bracket 72 and is secured on top by nut 111.

There are three positions in this embodiment for measuring shade. The first position is that depicted in FIGS. 5, 6, and 9. In this case, the bifurcated fiber optic cable 38 is positioned in a upward direction to monitor shade at an angle in the direction of movement of the continuous web of pile or napped material 12, e.g., carpeting. The bifurcated fiber optic cable 38 is substantially aligned with the longitudinal axis of the continuous web of pile or napped material 12 with the metal shield 96 positioned upward vertically and the positioning lever 108 is positioned downward vertically along the bifurcated fiber optic cable 38. The calibration plate 102 is positioned upward and to the right, as shown in FIG. 9, and outside the input of the bifurcated fiber optic cable 38.

The second position is that depicted in FIGS. 3, 4, and 10. In this case, the bifurcated fiber optic cable 38 is positioned in a downward direction to monitor shade at an angle in a direction against the movement of the continuous web of carpeting or napped material 12. The bifurcated fiber optic cable 38 is aligned with the longitudinal axis of the continuous web of carpeting or napped material 12 with the metal shield 96 positioned downward vertically and the positioning lever 108 is positioned upward vertically along with the bifurcated fiber optic cable 38. The calibration plate 102 is positioned upward and to the right, as before and as shown in FIG. 10, and outside the input of the bifurcated fiber optic cable 38. The positioning lever 108 triggers the first limit switch 84 in order to reverse the position of the bifurcated fiber optic cable 38 by substantially one hundred and eighty degrees. The positioning member 86 then oscillates by host computer, as shown in FIG. 2, between the first position of FIG. 9 and the second position of FIG. 10, thereby obtaining directional shade variation of the pile or napped materials 12, e.g., carpeting. This oscillation is accomplished with repeatable accuracy.

The third position is strictly for calibration purposes. As shown in FIGS. 7, 8, and 11, the bifurcated fiber optic cable 38 is perpendicularly aligned with respect to the longitudinal axis of the continuous web of pile or napped material 12, e.g., carpeting, with the metal shield 96 and the positioning bracket 85 attached to the bifurcated fiber optic cable 38 positioned across the pile or napped materials 12. The calibration plate 102 is positioned directly in the view of bifurcated fiber optic cable 38, as shown in FIG. 11. The positioning lever 108 of the positioning member 85 moves the position pole 114 thereby rotating the entire calibration plate 102 until the position pole 114 triggers the second limit switch 112. In this case the positioning lever 108 abuts the position pole 114 that abuts the second limit switch 112. The calibration plate 102 is preferably flat and of a consistent shade so that the shade measuring apparatus 20 can undergo repeatable, accurate measurements.

Referring now to FIGS. 12 and 13, an alternative preferred embodiment, due to greater design simplicity, also includes an L-shaped support member 266 mounted on a shade measuring support bracket 264. The L-shaped support member 266 is attached to the shade measuring support bracket 264 by a nut and bolt combination 268.

The bifurcated fiber optic cable 238 can be positioned at a fixed angle or a plurality of fixed angles in relation to the pile or napped fabric 12, e.g., carpeting, by any of a wide variety of mechanical support means. A specific example of a positioning member to support the bifurcated fiber optic cable 238 is that disclosed in FIGS. 12 and 13 and is generally indicated by numeral 286. The angle of the bifurcated fiber optic cable 238 in a plane normal to the pile or napped fabric 12, e.g., carpeting can range from zero to one hundred and eighty degrees and preferably range from thirty to one hundred and fifty degrees with an optimal angle of plus or minus forty-five degrees from the normal.

There is a stepper motor 274 mounted to the L-shaped support member 266 by means of a first pair of bolts 276. The stepper motor 274 has a rotatable axle 292 extending therefrom that is attached to a positioning bracket 285. Positioning bracket 285 is attached to rotatable axle 290 by means of set screw 288. A bifurcated fiber optic cable 238 is held in position by the positioning bracket 285 and is able to rotate in a position in that is directed upward in the direction of movement of the continuous web of pile or napped material 12, e.g., carpeting, and in a position in that is directed downward in the direction of movement of the continuous web of pile or napped material 12. The initial position is that depicted by FIGS. 12 and 13 in which the bifurcated fiber optic cable 238 is directed upward in the direction of movement of the continuous web of pile or napped material 12, e.g., carpeting. The next position is for the positioning bracket 285 to move downward until contact is made with a first limit switch 280 so that the bifurcated fiber optic cable 238 is directed downward against the direction of movement of the continuous web of pile or napped material 12, e.g., carpeting. The first limit switch 280 is attached the L-shaped support member 266 by means of a second pair of bolts 282.

The third position is a calibration position in which positioning member 286 moves upward until contact is made with a second limit switch 312 so that the bifurcated fiber optic cable 238 is directed against a calibration plate 302. In this situation, the bifurcated fiber optic cable 238 does not measure the shade of the continuous web of pile or napped material 12, e.g., carpeting. The second limit switch 312 is attached to the L-shaped support member 266 by means of a third pair of bolts 317.

There is a meter for measuring the amount of pile or napped material 12, e.g., carpeting, that is produced, which is generally indicated by numeral 350. Meter 350 has a pair of dual wheels 352 that are mounted on a shaft encoder 356 and secured by a pair of nuts 360. The shaft encoder 356 is attached to a pivoting arm 362 that is rotatably attached to an L-shaped support member 366 by means of bolt assembly 364 that is capable of providing a pivoting motion. The L-shaped support member 366 is attached to a metering support member 366 by means of dual bolt and nut combination 368. The shaft encoder 356 allows a map of the shade to be generated by the host computer 62, as shown in FIG. 2. The shaft encoder 356 is electrically connected to the host computer 62 by means of electrical wiring 358.

Another alternative embodiment is an apparatus to determine directional variation of shade of pile or napped materials covering a significant area such as broadloom carpeting as a typical non-limiting example. Referring now to FIGS. 14, 15, and 16, a rail system for determining directional variation of shade is generally indicated by numeral 401. This system 401 is defined by an I-beam 404 supported by a pair of support beams 406. A pair of bifurcated fiber optic cables are defined by numerals 414 and 415, respectively and are supported along I-beam 404 by an interconnected, linking cable carrier 418 comprising of oval elements 420 attached by a pair of dual pin members 422.

The pair of bifurcated fiber optic cables 414, 415 can be positioned at fixed angles from opposite directions in relation to the pile or napped fabric 412, e.g., broadloom carpeting, by any of a wide variety of mechanical support means. A specific example of positioning members to support the bifurcated fiber optic cables 414, 415 is that disclosed in FIGS. 14, 15, and 16 and is generally indicated by numeral 423. The angle of the bifurcated fiber optic cables 414, 415 in relation to the pile or napped fabric 412, e.g., broadloom carpeting can range from zero to plus or minus ninety degrees and preferably range from plus or minus fifteen degrees to plus or minus sixty degrees with the optimal angle as plus or minus forty-five degrees.

The pair of bifurcated fiber optic cables 414 and 415 are held in position at opposed downward angles into the broadloom carpet 412 by a pair of positioning brackets 424 and 425, respectively. Positioning bracket 424 is bolted into an inverted t-shaped carriage mechanism 427 by a first pair of bolts 429, as shown in FIG. 16, and positioning bracket 425 is bolted into the inverted t-shaped carriage mechanism 427 by a second pair of bolts 430. Located within the inverted t-shaped carriage mechanism 427 on the same side as positioning member 425 is a first pair of carriage drive wheels 432 and 433, respectively that are rotatably attached to the inverted t-shaped carriage mechanism 427 by means of a pair of bolts 435 and 436, respectively. There is a support bracket 440 that is attached to the inverted t-shaped carriage mechanism 427 by means of the bolt 436 and attached to the interconnected linking raceway 418 by means of bolt and nut combination 421. Located within the inverted t-shaped carriage mechanism 427 on the same side as positioning bracket 424 is a second pair of carriage drive wheels 444 (shown) and 445 (not shown), respectively that are rotatably attached to the inverted t-shaped carriage mechanism 427 by means of a pair of bolts (not shown) in the same manner that the first pair of carriage drive wheels 432 and 433 are attached.

There is an belt 450, as shown in FIG. 14 and FIG. 16, that is powered by a first pulley 452 attached to a stepper motor 454. The stepper motor 454 is attached to I-beam 404 by means of a series of four bolts 456. The belt 450 loops around a second pulley 458 that is located at the opposite end of the I-beam 404 and rotatably attached thereto by bolt 497 a chain and sprocket wheel is construed as the equivalent to a pulley and a belt. The belt 450 is attached to the inverted t-shaped carriage mechanism 427 by attachment mechanism 499 at both ends, as shown in FIG. 16, thereby moving the inverted t-shaped carriage mechanism 427 along the I-beam 404 so that shade measurements are made at opposite positions and directions on the broadloom carpet 412 by two bifurcated fiber optic cables 414 and 415, respectively. As shown in FIG. 14, there is a first limit switch 490 on the one end of the I-beam 404 and a second limit switch 492 on the other end of I-beam 404 to stop and reverse direction of the inverted t-shaped carriage mechanism 427.

The optimal embodiment, with regard to obtaining directional shade variation data, is that detailed in FIG. 17, wherein pile or napped fabric 475, e.g., carpeting in the form of broadloom or carpet tile is the utilization of four bifurcated fiber cables 478, 479, 480, and 481 extending in all four directions to provide the shade variation in all four directions simultaneously. The pile or napped fabric 475 is transported by a conveyor 467.

A flow chart that describes the process steps utilized in the software for determining directional variation of shade of carpeting or napped materials that are formed or bonded is depicted in FIGS. 18 and 19. The initial start step is depicted in the Block designated by numeral 502. The next step is an initialization routine that is depicted by Block 504 and includes clearing memory, loading motor controller codes into an array, loading ninety-seven potent CIE laboratory functions into an array, enabling user option keys, enabling error trapping for communications, displaying the menu for the operator, and initializing communications with spectrophotometers, yardage counter, and motor controller.

The third step is to determine if calibration utilizing a one hundred percent reference shade has occurred and this step is depicted by Block 506. If calibration is yet to occur, the bifurcated fiber optic cable 38 is positioned to determine the shade of the calibration plate 102, as shown in FIGS. 7, 8, and 11, which is depicted by Block 508. The next step is to poll the spectrophotometers for spectral data, as shown in Block 510, and store these responses as one hundred percent reference values, as shown in Block 512. The L, a, and b values, yardage, and north/south position are saved to a data log file and this is depicted by Block 514. The next step is to determine if an automatic calibration is required as depicted by Block 516. If this is affirmative, then Blocks 508, 510, and 512 are repeated. These steps include positioning the bifurcated fiber optic cable 38 to determine the shade of the calibration plate 102, as shown in FIGS. 7, 8, and 11, polling the spectrophotometers for spectral data and storing these responses as one hundred percent reference values. If automatic calibration is not required, then a determination is made to see if the process should be continued as indicated by Block 518.

If the process is merely continued, then this is accomplished by moving the motor and thereby moving the probes one hundred and eighty degrees to the next position. This is a clockwise motion from north to south and a counterclockwise motion from south to north. This step is indicated by Block 520.

The next step is to poll the spectrophotometers for spectral data and poll the yardage counter for material traversed, as indicated by the step denoted by Block 530. L, a, and b values are then computed on both sides, as denoted by Block 532, with the average values developed for a fixed time period that is preferably between twenty to forty seconds. The L, a, and b values are then saved as well as the yardage and a north/south position to a data log file, Block 514. If an automatic calibration is not required, Block 516, and continuation of the determination of shade for this particular carpet or napped material is not desired, Block 518, then the operator through the software menu can enter a new style, pattern, dye lot, machine, L, a and b tolerances and time between shade readings into the computer as a step depicted by Block 522. The next step is to create a data log file, Block 524, reset the yardage counter, Block 526, and move to the north positions on both sides of a carpet bonding machine, Block 528.

Then the spectrophotometers are polled for spectral data and the yardage counter is polled for material traversed, as indicated by the step denoted by Block 530. L, a, and b values are then computed on both sides, as denoted by Block 532, with the average values developed for a fixed time period that is preferably between twenty to forty seconds. The L, a, and b values are then saved as well as the yardage and a north/south position to a data log file, as shown in Block 514. If an automatic calibration is not required, Block 516, then continuation of the determination of shade for this particular pile or napped material will be accomplished by repeating Blocks 530, 532, 514, 516, and 518 until shade has been accurately determined for the specific carpet or napped material product. If a new type of pile or napped fabric is utilized, then Blocks 522, 524, 526, and 528 must be repeated prior to Blocks 530, 532, 514, 516, and 518.

A flow chart that describes the process steps utilized in the software for determining directional variation of shade of a large area of pile or napped materials, e.g., broadloom carpeting, by means of scanning is depicted in FIGS. 20 and 21. The initial start step is depicted by Block 550. The next step is an initialization routine that is depicted by Block 552 and includes clearing the memory, loading motor controller codes into an array, loading ninety-seven point CIE laboratory functions into an array, enabling user option keys, displaying the menu for an operator, enabling communications for error trapping, and initializing communications with spectrophotometers, yardage counter, and motor controller.

The third step is to determine if automatic calibration utilizing a one hundred percent reference shade and a zero percent reference shade has occurred and this step is depicted by Block 554. If automatic calibration is desired, then bifurcated fiber optic cable 438 is positioned over a zero percent shade reference material and a hundred percent shade reference material. This step is depicted by Block 558.

The next step, Block 560, is to read and update reference spectral data files.

The next step, Block 562, is for the operator to enter a style, pattern, dye lot, machine, and L, a and b tolerances through a menu. If automatic calibration was not desired and was previously performed, then you may skip Blocks 558 through 560 and go directly to Block 562 if you open the zero percent and one hundred percent spectral reference calibration files and copy to arrays as indicated by Block 556.

The next step is numerically depicted as Block 564 and involves resetting the yardage counter while Block 566 involves either positioning a shade determination probe manually or initiating a scanning sequence for left, center, and right positions.

Then the spectrophotometers are polled for spectral data and the yardage counter is polled for material traversed, as indicated by the step denoted by Block 568. L, a, and b values are then computed for a single reading, as denoted by Block 570, in conjunction with saving data and position with average values developed for a fixed position. Block 572 involves the determination if more readings are needed at that same location. If more readings are needed at that same location, then Block 570 is repeated until this is no longer the situation.

When no more readings are needed in Block 572, then a determination is made in Block 574 if additional scanning should be done. If this is positive, then a determination is made if calibration is required in Block 576. If the determination is negative with regard to calibration, then the bifurcated fiber optic cable 414, 415 moves to the next position, Block 578, and Blocks 568, 570, 572, 574 and 576 are repeated. This involves polling the spectrophotometers for spectral data and the yardage counter is polled for material traversed and computing L, a, and b values for a single reading in conjunction with saving data and position with average values developed for a fixed position and determining if more readings are needed at the same location and if continued scanning is required and if calibration is required.

If the determination is made in Block 574 that no further scanning is required, then Blocks 562, 564, 566, 568, 570, and 572 are repeated. These include an operator entering a style, pattern, dye lot, machine, and L, a and b tolerances through a software menu and resetting the yardage counter. This also includes either positioning a shade determination probe manually or initiating a scanning sequence for left, center, and right positions. Then the spectrophotometers are polled for spectral data and the yardage counter is polled for material traversed. L, a, and b values are then computed for a single reading in conjunction with saving data and position with average values developed for a fixed position. A determination is made if more readings are needed at same location. If more readings are needed at the same location, then Block 570 is repeated until this is no longer the case.

If calibration is required in Block 576, a determination is made in Block 554 if automatic calibration is required. If calibration is desired and has yet to occur, the bifurcated fiber optic cable 38 is positioned over a zero percent shade reference material and a hundred percent shade reference material, which is depicted by Block 558. The next step, Block 560, is to read and update reference spectral data files.

The next step, Block 562, is for the operator to enter a style, pattern, dye lot, machine, and L, a and b tolerances through a software menu. If automatic calibration was previously performed, then you may skip from Block 554 and go directly to Block 562 if you open the zero percent and one hundred percent spectral reference calibration files and copy to arrays as indicated by Block 556.

The next step is numerically depicted as Block 564 and involves resetting the yardage counter while Block 566 involves either positioning a shade determination probe manually or initiating a scanning sequence for left, center, and right positions.

Then the spectrophotometers are polled for spectral data and the yardage counter is polled for material traversed, as indicated by the step denoted by Block 568. L, a, and b values are then computed for a single reading, as denoted by Block 570, in conjunction with saving data and position with average values developed for a fixed position. Block 572 involves the determination if more readings are needed at that same location. If more readings are needed at that same location, then Block 570 is repeated until this is no longer the situation.

When no more readings are needed in Block 572, then a determination is made in Block 574 if additional scanning should be done. If this is positive, then a determination is made if calibration is required in Block 576. If the determination is negative with regard to calibration, then the bifurcated fiber optic cable 414, 415 moves to the next position, Block 578, and Blocks 568, 570, 572, 574 and 576 are repeated. This involves polling the spectrophotometers for spectral data and the yardage counter is polled for material traversed and computing L, a, and b values for a single reading in conjunction with saving data and position with average values developed for a fixed position and determining if more readings are needed at the same location and if continued scanning is required and if calibration is required.

From the foregoing, it will be apparent to those skilled in the art that various modifications in the above described devices can be made without departing from the spirit and scope of the invention. Accordingly the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein. In particular, there can be a wide variety of means of robotically positioning bifurcated fiber optic cables attached to spectrophotometers.

What is claimed is:

1. An apparatus for measuring directional variation of shade of pile or napped textile materials which comprises:
   (a) a spectrophotometer;
   (b) a bifurcated fiber optic cable, having a first portion and a second portion, wherein said first portion of said bifurcated fiber optic cable is connected to said sprectrophotometer; and
   (c) a positioning mechanism that is operatively attached to said second portion of said bifurcated fiber optic cable for rotating said bifurcated fiber optic cable in a plurality of angles with respect to said textile materials, whereby said spectrophotometer shines light through said bifurcated fiber optic cable against said textile materials and said spectrophotometer receives reflected light from said textile materials through said bifurcated fiber optic cable at said plurality of angles to measure directional variation of shade of said pile or napped textile materials.

2. An apparatus for measuring directional variation of shade of pile or napped textile materials which comprises:
   (a) a plurality of spectrophotometers;
   (b) a plurality of bifurcated fiber optic cables, each having a first portion and a second portion, wherein each of said first portions of said bifurcated fiber optic cables are connected to each of said spectrophotometers; and
   (c) a plurality of positioning mechanisms that are operatively attached to each of said second portions of said bifurcated fiber optic cables for rotating each of said plurality of bifurcated fiber optic cables in a plurality of angles with respect to said textile materials, whereby each of said plurality of spectrophotometers shines light through each of said bifurcated fiber optic cables against said textile materials and each of said plurality of spectrophotometers receives reflected light from said textile materials through each of said plurality of bifurcated fiber optic cables each at said plurality of angles to measure directional variation of shade of said pile or napped textile materials.

3. An apparatus for measuring directional variation of shade of pile or napped textile materials which comprises:
   (a) a first spectrophotometer;
   (b) a first bifurcated fiber optic cable, having a first portion and a second portion, wherein said first portion of said first bifurcated fiber optic cable is connected to said first spectrophotometer;
   (c) a first positioning mechanism that is operatively attached to said second portion of said bifurcated fiber optic cable for rotating said first bifurcated fiber optic cable in a plurality of angles with respect to said textile materials, whereby said first spectrophotometer shines light through said first bifurcated fiber optic cable against said textile materials and said first spectrophotometer receives reflected light from said textile materials through said first bifurcated fiber optic cable at said plurality of angles to measure directional variation of shade of said pile or napped textile materials;
   (d) a second spectrophotometer;
   (e) a second bifurcated fiber optic cable, having a first portion and a second portion, wherein said first portion of said second bifurcated fiber optic cable is connected to said second spectrophotometer; and
   (f) a second positioning mechanism that is operatively attached to said second portion of said second bifurcated fiber optic cable for rotating said second bifurcated fiber optic cable in a plurality of angles with respect to said textile materials, whereby said second spectrophotometer shines light through said second bifurcated fiber optic cable against said textile materials and said second spectrophotometer receives reflected light from said textile materials through said second bifurcated fiber optic cable at said plurality of angles to measure directional variation of shade of said pile or napped textile materials.

4. An apparatus for measuring directional variation of shade of pile or napped textile materials which comprises:
   (a) a first spectrophotometer;
   (b) a first bifurcated fiber optic cable, having a first portion and a second portion, wherein said first portion of said first bifurcated fiber optic cable is connected to said first spectrophotometer;
   (c) a first positioning mechanism that is operatively attached to said second portion of said bifurcated fiber optic cable for rotating said first bifurcated fiber optic cable in a plurality of angles with respect to said textile materials, whereby said first spectrophotometer shines light through said first bifurcated fiber optic cable against said textile materials and said first spectrophotometer receives reflected light from said textile materials through said first bifurcated fiber optic cable at said plurality of angles to measure directional variation of shade of said pile or napped textile materials;

(d) a second spectrophotometer;

(e) a second bifurcated fiber optic cable, having a first portion and a second portion, wherein said first portion of said second bifurcated fiber optic cable is connected to said second spectrophotometer;

(f) a second positioning mechanism that is operatively attached to said second portion of said second bifurcated fiber optic cable for rotating said second bifurcated fiber optic cable in a plurality of angles with respect to said textile materials, whereby said second spectrophotometer shines light through said second bifurcated fiber optic cable against said textile materials and said second spectrophotometer receives reflected light from said textile materials through said second bifurcated fiber optic cable at said plurality of angles to measure directional variation of shade of said pile or napped textile materials;

(g) a third spectrophotometer;

(h) a third bifurcated fiber optic cable, having a first portion and a second portion, wherein said first portion of said third bifurcated fiber optic cable is connected to said third spectrophotometer;

(i) a third positioning mechanism that is operatively attached to said second portion of said third bifurcated fiber optic cable for rotating said third bifurcated fiber optic cable in a plurality of angles with respect to said textile materials, whereby said third spectrophotometer shines light through said third bifurcated fiber optic cable against said textile materials and said third spectrophotometer receives reflected light from said textile materials through said third bifurcated fiber optic cable at said plurality of angles to measure directional variation of shade of said pile or napped textile materials;

(j) a fourth spectrophotometer;

(k) a fourth bifurcated fiber optic cable, having a first portion and a second portion, wherein said first portion of said fourth bifurcated fiber optic cable is connected to said fourth spectrophotometer; and (l) a fourth positioning mechanism that is operatively attached to said second portion of said fourth bifurcated fiber optic cable for rotating said fourth bifurcated fiber optic cable in a plurality of angles with respect to said textile materials, whereby said fourth spectrophotometer shines light through said fourth bifurcated fiber optic cable against said textile materials and said fourth spectrophotometer receives reflected light from said textile materials through said fourth bifurcated fiber optic cable at said plurality of angles to measure directional variation of shade of said pile or napped textile materials.

5. An apparatus for measuring directional variation of shade of pile or napped textile materials as defined in claim 1, wherein said positioning mechanism includes bracket attached to said bifurcated fiber optic cable and a motorized mechanism for rotating said bracket into said plurality of angles operatively attached to said bracket and a control mechanism operatively attached to said motorized mechanism for precise, repeatable positioning of said bifurcated fiber optic cable.

6. An apparatus for measuring directional variation of shade of pile or napped textile materials as defined in claim 5, wherein said motorized mechanism includes a stepper motor.

7. An apparatus for measuring directional variation of shade of pile or napped textile materials as defined in claim 6, further comprising a frame for supporting said stepper motor.

8. An apparatus for measuring directional variation of shade of pile or napped textile materials as defined in claim 5, wherein said control mechanism includes a computer.

9. An apparatus for measuring directional variation of shade of pile or napped textile materials as defined in claim 5, wherein said control mechanism includes at least one limit switch.

10. An apparatus for measuring directional variation of shade of a moving web of pile or napped textile materials which comprises:

(a) a spectrophotometer;

(b) a bifurcated fiber optic cable, having a first portion and a second portion, wherein said first portion of said bifurcated fiber optic cable is connected to said spectrophotometer;

(c) a positioning mechanism that is operatively attached to said second portion of said bifurcated fiber optic cable for rotating said bifurcated fiber optic cable in a plurality of angles with respect to said moving web of textile materials, whereby said spectrophotometer shines light through said bifurcated fiber optic cable against said moving web of textile materials and said spectrophotometer receives reflected light from said moving web of textile materials through said bifurcated fiber optic cable at said plurality of angles to measure directional variation of shade of said pile or napped textile materials; and (d) a counter that is in frictional contact with said moving web of textile materials, whereby said counter counts the number of yards of said moving web of textile materials that traverse past said bifurcated fiber optic cable.

11. An apparatus for measuring directional variation of shade of pile or napped textile materials as defined in claim 10, wherein said positioning mechanism includes a bracket attached to said bifurcated fiber optic cable and a motorized mechanism for rotating said bracket into said plurality of angles operatively attached to said bracket and a control mechanism operatively attached to said motorized mechanism for precise, repeatable positioning of said bifurcated fiber optic cable.

12. An apparatus for measuring directional variation of shade of pile or napped textile materials as defined in claim 11, wherein said motorized mechanism includes a stepper motor.

13. An apparatus for measuring directional variation of shade of pile or napped textile materials as defined in claim 12, further comprising a frame for supporting said stepper motor.

14. An apparatus for measuring directional variation of shade of pile or napped textile materials as defined in claim 11, wherein said control mechanism includes a computer.

15. An apparatus for measuring directional variation of shade of pile or napped textile materials as defined in claim 11, wherein said control mechanism includes at least one limit switch.

16. An apparatus for measuring directional variation of shade of pile or napped textile materials which comprises:

(a) a spectrophotometer;

(b) a bifurcated fiber optic cable, having a first portion and a second portion, wherein said first portion of said bifurcated fiber optic cable is connected to said spectrophotometer;

(c) a positioning mechanism that is operatively attached to said second portion of said bifurcated fiber optic cable for rotating said bifurcated fiber optic cable in a plurality of angles with respect to said moving web of textile materials, whereby said spectrophotometer shines light through said bifurcated fiber optic cable against said moving web of textile materials and said spectrophotometer receives reflected light from said moving web of textile materials through said bifurcated fiber optic cable at said plurality of angles to measure directional variation of shade of said pile or napped textile materials; and (d) a calibration plate whereby said positioning mechanism can position said bifurcated fiber optic so that said spectrophotometer shines light through said bifurcated fiber optic cable against said calibration plate so that said spectrophotometer receives reflected light from said calibration plate through said bifurcated fiber optic cable, in order to calibrate said spectrophotometer.

17. An apparatus for measuring directional variation of shade of pile or napped textile materials as defined in claim 16, wherein said positioning mechanism includes a bracket attached to said bifurcated fiber optic cable and a motorized mechanism for rotating said bracket into said plurality of angles operatively attached to said bracket and a control mechanism operatively attached to said motorized mechanism for precise, repeatable positioning of said bifurcated fiber optic cable.

18. An apparatus for measuring directional variation of shade of pile or napped textile materials as defined in claim 17, wherein said bracket includes a finger and said calibration plate includes a pole and further includes a means to selectively move said finger to contact said pole to position said calibration plate and said bifurcated fiber optic cable so that reflected light is received into said bifurcated fiber optic cable from said spectrophotometer shines light through said bifurcated fiber optic cable against said calibration plate so that said spectrophotometer receives reflected light from said calibration plate through said bifurcated fiber optic cable, in order to calibrate said spectrophotometer.

19. An apparatus for measuring directional variation of shade of pile or napped textile materials as defined in claim 17, wherein said motorized mechanism includes a stepper motor.

20. An apparatus for measuring directional variation of shade of pile or napped textile materials as defined in claim 19, further comprising a frame for supporting said stepper motor.

21. An apparatus for measuring directional variation of shade of pile or napped textile materials as defined in claim 17, wherein said control mechanism includes a computer.

22. An apparatus for measuring directional variation of shade of pile or napped textile materials as defined in claim 17, wherein said control mechanism includes at least one limit switch.

23. An apparatus for measuring directional variation of shade of a moving web pile or napped textile materials having a longitudinal axis which comprises:

(a) a first spectrophotometer;

(b) a first bifurcated fiber optic cable, having a first portion and a second portion, wherein said first portion of said first bifurcated fiber optic cable is connected to said first spectrophotometer;

(c) a second spectrophotometer;

(d) a second bifurcated fiber optic cable, having a first portion and a second portion, wherein said first portion of said second bifurcated fiber optic cable is connected to said second spectrophotometer;

(e) a carriage mechanism having said second portion of said first bifurcated fiber optic cable mounted thereto and said second portion of said second bifurcated fiber optic cable mounted thereto; and (f) a drive mechanism operatively connected to said carriage mechanism for moving said carriage mechanism along a track, whereby said first spectrophotometer shines light through said first bifurcated fiber optic cable against said moving web of textile materials and said first spectrophotometer receives reflected light from said moving web of textile materials through said first bifurcated fiber optic cable at a first angle and said second spectrophotometer shines light through said second bifurcated fiber optic cable against said moving web of textile materials and said second spectrophotometer receives reflected light from said moving web of textile materials through said second bifurcated fiber optic cable at a second angle and said shade measured at said first angle and said second angle provide said directional variation of shade of said pile or napped textile materials.

24. An apparatus for measuring directional variation of shade of a moving web pile or napped textile materials having a longitudinal axis as defined in claim 23, wherein said drive mechanism includes a motor attached to a first sprocket wheel and including a chain that is in frictional contact with said first sprocket wheel and a rotatable second sprocket wheel wherein said chain is attached to said carriage mechanism for moving said carriage mechanism along said track.

25. An apparatus for measuring directional variation of shade of a moving web pile or napped textile materials having a longitudinal axis as defined in claim 23, wherein said drive mechanism includes a motor attached to a first pulley and including a belt that is in frictional contact with said first pulley and a rotatable second pulley wherein said belt is attached to said carriage mechanism for moving said carriage mechanism along said track.

26. An apparatus for measuring directional variation of shade of a moving web pile or napped textile materials having a longitudinal axis as defined in claim 23, wherein said track includes an I-beam member.

27. An apparatus for measuring directional variation of shade of a moving web pile or napped textile materials having a longitudinal axis as defined in claim 26, wherein said carriage mechanism includes at least one wheel on each side of said I-beam member.

28. An apparatus for measuring directional variation of shade of a moving web pile or napped textile materials having a longitudinal axis as defined in claim 23, wherein said track includes a plurality of limit switches.

29. A process for measuring directional variation of shade of pile or napped textile materials which comprises the step of measuring shade of said textile materials from a plurality of angles by sequentially positioning a bifurcated fiber optic cable in relation to said textile materials and said bifurcated fiber optic cable is connected to a spectrophotometer, whereby said spectrophotometer shines light through said bifurcated fiber optic cable against said textile materials and said spectrophotometer receives reflected light from said textile materials through said bifurcated fiber optic cable at said plurality of angles to measure directional variation of shade of said pile or napped textile materials.

30. A process for measuring directional variation of shade of pile or napped textile materials which comprises the steps of:

(a) measuring shade of said textile materials from a first angle by positioning a bifurcated fiber optic cable in relation to said textile materials and said bifurcated fiber optic cable is connected to a spectrophotometer, whereby said spectrophotometer shines light through said bifurcated fiber optic cable against said textile materials and said spectrophotometer receives reflected light from said textile materials through said bifurcated fiber optic cable at said first angle; and (b) measuring shade of said textile materials from a second angle by positioning a bifurcated fiber optic cable in relation to said textile materials and said bifurcated fiber optic cable is connected to a spectrophotometer, whereby said spectrophotometer shines light through said bifurcated fiber optic cable against said textile materials and said spectrophotometer receives reflected light from said textile materials through said bifurcated fiber optic cable and said shade measured at said first angle and said second angle provide said directional variation of shade of said pile or napped textile materials.

31. A process for measuring directional variation of shade of pile or napped textile materials which comprises the steps of:

(a) measuring shade of said textile materials from a first angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said first angle and said spectrophotometer receives reflected light from said textile materials through said bifurcated fiber optic cable at said first angle;

(b) measuring shade of said textile materials from a second angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said second angle and said spectrophotometer receives reflected light from said textile materials through said bifurcated fiber optic cable at said second angle;

(c) measuring shade of said textile materials from a third angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said third angle and said spectrophotometer receives reflected light from said textile materials through said bifurcated fiber optic cable at said third angle;

(d) measuring shade of said textile materials from a fourth angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said fourth angle and said spectrophotometer receives reflected light from said textile materials through said bifurcated fiber optic cable at said fourth angle and said shade measured at said first angle and said second angle and said third angle and said fourth angle provide said directional variation of shade of said pile or napped textile materials.

32. A process for measuring directional variation of shade of pile or napped textile materials which comprises the steps of:

(a) measuring shade of a calibration plate by positioning a bifurcated fiber optic cable in relation to said calibration plate whereby said bifurcated fiber optic cable is connected to a spectrophotometer, whereby said spectrophotometer shines light through said bifurcated fiber optic cable against said calibration plate and said spectrophotometer receives reflected light from said calibration plate through said bifurcated fiber optic cable;

(b) measuring shade of said textile materials from a first angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said first angle and said spectrophotometer receives reflected light from said textile materials through said bifurcated fiber optic cable at said first angle; and (c) measuring shade of said textile materials from a second angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said second angle and said spectrophotometer receives reflected light from said textile materials through said bifurcated fiber optic cable at said second angle and said shade measured at said first angle and said second angle provide said directional variation of shade of said pile or napped textile materials.

33. A process for measuring directional variation of shade of pile or napped textile materials which comprises the steps of:

(a) moving a calibration plate in a position so that a spectrophotometer shines light through a bifurcated fiber optic cable against said calibration plate and said spectrophotometer receives reflected light from said calibration plate through said bifurcated fiber optic cable, thereby measuring shade of said calibration plate;

(b) measuring shade of said textile materials from a first angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said first angle and said spectrophotometer receives reflected light from said textile materials through said bifurcated fiber optic cable at said first angle; and (c) measuring shade of said textile materials from a second angle by positioning a bifurcated fiber optic cable in relation to said textile materials whereby said bifurcated fiber optic cable is connected to a spectrophotometer, whereby said spectrophotometer shines light through said bifurcated fiber optic cable against said textile materials at said second angle and said spectrophotometer receives reflected light from said textile materials through said bifurcated fiber optic cable at said second angle and said shade measured at said first angle and said second angle provide said directional variation of shade of said pile or napped textile materials.

34. A process for measuring directional variation of shade of a moving web of pile or napped textile materials, having a longitudinal axis, which comprises the steps of:

(a) measuring shade of said textile materials from a plurality of angles by positioning a plurality of bifurcated fiber optic cables in relation to said textile materials whereby said bifurcated fiber optic cables are connected to a plurality of spectrophotometers and are mounted on a carriage, whereby said plurality of spectrophotometers shine light through said plurality of bifurcated fiber optic cables against said moving web of textile materials at said plurality of angles and said plurality of spectrophotometers receive reflected light from said moving web of textile materials through said plurality of bifurcated fiber optic cables at said plurality of angles to measure directional variation of shade of said pile or napped textile materials; and (b) moving said carriage along a track transversely with respect to said longitudinal axis of said moving web of textile materials.

35. A process for measuring directional variation of shade of a moving web of pile or napped textile materials, having a longitudinal axis, which comprises the steps of:

(a) measuring shade of said textile materials from a plurality of angles by positioning a plurality of bifurcated fiber optic cable in relation to said textile materials whereby said bifurcated fiber optic cables are connected to a plurality of spectrophotometers and are mounted on a carriage having at least a pair of wheels, whereby said plurality of spectrophotometers shine light through said plurality of bifurcated fiber optic cables against said moving web of textile materials at said plurality of angles and said plurality of spectrophotometers receive reflected light from said moving web of textile materials through said plurality of bifurcated fiber optic cables at said plurality of angles to measure directional variation of shade of said pile or napped textile materials; and (b) moving said carriage on an I-beam track transversely with respect to said longitudinal axis of said moving web of textile materials.

36. A process for measuring directional variation of shade of a moving web of pile or napped textile materials, having a longitudinal axis, which comprises the steps of:

(a) measuring shade of said textile materials from a plurality of angles by positioning a plurality of bifurcated fiber optic cables in relation to said moving web of textile materials whereby said bifurcated fiber optic cables are connected to a plurality of spectrophotometers and are mounted on a carriage having at least a pair of wheels, whereby said plurality of spectrophotometers shine light through said plurality of bifurcated fiber optic cables against said moving web of textile materials at said plurality of angles and said plurality of spectrophotometers receive reflected light from said moving web of textile materials through said plurality of bifurcated fiber optic cables at said plurality of angles to measure directional variation of shade of said pile or napped textile materials; and (b) moving said carriage on an I-beam track transversely with respect to said longitudinal axis of said moving web of textile materials by means of a chain that is in frictional contact with both a first sprocket that is attached to a motor and a second rotatable sprocket wherein said chain is attached to said carriage.

37. A process for measuring directional variation of shade of a moving web of pile or napped textile materials, having a longitudinal axis, which comprises the steps of:

(a) measuring shade of said textile materials from a plurality of angles by positioning a plurality of bifurcated fiber optic cables in relation to said moving web of textile materials whereby said bifurcated fiber optic cables are connected to a plurality of spectrophotometers and are mounted on a carriage having at least a pair of wheels, whereby said plurality of spectrophotometers shine light through said plurality of bifurcated fiber optic cables against said moving web of textile materials at said plurality of angles and said plurality of spectrophotometers receive reflected light from said moving web of textile materials through said plurality of bifurcated fiber optic cables at said plurality of angles to measure directional variation of shade of said pile or napped textile materials; and (b) moving said carriage on an I-beam track transversely with respect to said longitudinal axis of said moving web of textile materials by means of a chain that is in frictional contact with both a first sprocket that is attached to a motor and a second rotatable sprocket wherein said chain is attached to said carriage.

\* \* \* \* \*